United States Patent [19]
Guth et al.

[11] Patent Number: 4,576,757
[45] Date of Patent: Mar. 18, 1986

[54] PROCESS FOR THE PREPARATION OF MONOACYL POLYALKYLENE POLYAMINES

[75] Inventors: Jacob J. Guth, Upper Black Eddy, Pa.; Elvin R. Lukenbach, Somerset; Richard R. Tenore, Martinsville, both of N.J.

[73] Assignee: Johnson & Johnson Baby Products Company, New Brunswick, N.J.

[21] Appl. No.: 604,267

[22] Filed: Apr. 26, 1984

[51] Int. Cl.[4] ............................................. C07C 102/00
[52] U.S. Cl. ................................................... 260/404.5
[58] Field of Search ............................. 260/404.5 PA

[56] References Cited

U.S. PATENT DOCUMENTS 1,947,951 2/1934 Neelmeir et al. ............... 260/404.5

OTHER PUBLICATIONS

Baltzly et al., "The Aminolysis of Esters, A Preliminary Study", *J. Amer. Chem. Soc.*, 9/1950, pp. 4149–4152.
Betts and Hammett, "A Kinetic Study of the Ammonolysis of Phenylacetic Ester in Methanol Solution", *J. Amer. Chem. Soc.*, 1937, pp. 1568–1572.

*Primary Examiner*—Charles F. Warren
*Assistant Examiner*—Elizabeth A. Flaherty
*Attorney, Agent, or Firm*—Steven P. Berman

[57] ABSTRACT

A process for the preparation of monoacyl polyalkylene polyamines comprising reacting a fatty acid ester with a polyalkylene polyamine in the presence of a suitable hydroxylic solvent.

5 Claims, No Drawings

PROCESS FOR THE PREPARATION OF MONOACYL POLYALKYLENE POLYAMINES

BACKGROUND OF THE INVENTION

The present invention relates to a process for the preparation of monoacyl polyalkylene polyamines. The monoacyl polyalkylene polyamines which can be prepared by the present process may be represented by the formula $$R-\overset{O}{\underset{\|}{C}}-NH(X-NH)_nH$$

wherein R is straight or branched chain alkyl of from 7 to 21 carbon atoms or mixtures thereof, n is an integer of from 1 to 3 and X is straight or branched chain alkylene or hydroxyalkylene of from 2 to 6 carbon atoms.

The prior art shows many processes for combining amines and fatty acids or esters. Reactions that are satisfactory when amines are involved are often unsatisfactory when diamines are combined with a fatty acid or ester. When diamines are involved, the processes are more complex and more difficult to control as a result of the formation of various side products. See, for example, U.S. Pat. No. 1,947,951, 2,387,201 and 2,750,366. In an article entitled "The Aminolysis of Esters. A Preliminary Study", J. Am. Chem. Soc., 72:4149 (1950), Baltzly et al., reported the results of aminolysis of esters utilizing monoamines in the presence of solvents including alcoholic solvents. Monoacyl polyalkylene polyamines can be prepared by reacting a suitable fatty acid or ester with a diamine at elevated temperatures, e.g., 100°–250° C. for a period of several hours. This reaction can be shown schematically when ethylenediamine is utilized as follows:

$$R-\overset{O}{\underset{\|}{C}}-OM + NH_2-CH_2CH_2-NH_2 \xrightarrow{100°-250° C.}$$

$$R-\overset{O}{\underset{\|}{C}}-NH-CH_2CH_2-NH_2 +$$

$$R-\overset{O}{\underset{\|}{C}}-NH-CH_2CH_2-NH-\overset{O}{\underset{\|}{C}}-R$$

Although this process results in the preparation of some of the desired end-product, there is significant contamination of the end-product with undesirable diamide by-products which must be separated out. There may also be off-color and malodor problems as a result of the high temperatures required. Furthermore, due to the temperatures required, the process is energy inefficient and expensive.

It is, therefore, an object of this invention to provide a novel process for the preparation of monoacyl polyalkylene polyamines.

It is a further object of this invention to provide a process for the preparation of monoacyl polyalkylene polyamines which results in good yields and low diamide contamination.

It is a still further object of the present invention to provide a process for the preparation of monoacyl polyalkylene polyamines which can be carried out at relatively low temperatures and is, therefore, energy efficient.

Other objects and advantages of the present invention will be set forth in or apparent from the following description.

SUMMARY OF THE INVENTION

The foregoing objects are achieved by reacting a suitable fatty acid ester with a polyalkylene polyamine in the presence of a suitable hydroxylic solvent to yield the desired monoacyl polyalkylene polyamine. The polyalkylene polyamine and fatty acid ester should be present in a ratio of from about 25:1 to 5:1, preferably about 20:1 to 10:1. The suitable hydroxylic solvents include the lower alcohols such as methanol, ethanol and propanol with the preferred solvent being methanol. The solvent should be present in an amount of from about 5 to 40% by weight of the total weight of the reaction mixture. The reaction should be carried out at temperatures of from about 20° to 80° C., preferably about 40° to 50° C. If the reaction is carried out under pressure, low diamide contamination is observed at higher temperatures and the rate of the reaction remains favorable.

The general reaction of the present invention can be illustrated schematically as follows:

$$R_1\overset{O}{\underset{\|}{C}}-OR_2 + H_2N(X-NH)_nH \longrightarrow R_1\overset{O}{\underset{\|}{C}}-NH(X-NH)_nH$$

wherein $R_1$ is alkyl containing from about 7 to 21 carbon atoms or mixtures thereof, $R_2$ is lower alkyl containing from about 1 to 3 carbon atoms, n is an integer of from 1 to 3 and X is straight or branched chain alkylene or hydroxyalkylene containing from 2 to 6 carbon atoms.

It has been unexpectedly found that by carrying out this reaction in a specific hydroxylic solvent and at low temperatures, the quantity of undesirable by-products is greatly reduced and the desired monoacyl polyalkylene polyamine has improved color and odor properties. The process also consumes less energy and utilizes less elaborate equipment when carried out in this manner due to the lower temperatures that may be utilized, if desired. If the reaction is carried out at higher temperatures under pressure, more elaborate equipment is required and more energy will be consumed, but the other advantages of the invention will still be achieved.

The resulting monoacyl polyalkylene polyamines can be utilized as surface active agents in various personal care and industrial applications. These compounds are also useful as intermediates for the production of known useful surface active agents. For example, a monoacyl polyalkylene polyamine of the structure $$CH_3(CH_2)_{10}\overset{O}{\underset{\|}{C}}-NH-CH_2CH_2-NH_2$$

can be reacted with ethylene chlorohydrin followed by reaction with sodium monochloroacetate in alkaline aqueous medium to yield lauroamphoglycinate of the structure

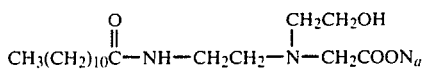

This compound and related compounds are shown in the CTFA Cosmetic Ingredient Dictionary and are available as surface active agents for use in personal care formulations from a number of commercial sources.

The following examples will illustrate in detail the manner in which the present invention may be practiced. It will be understood, however, that the invention is not confined to the specific limitations set forth in the individual examples, but rather to the scope of the appended claims.

EXAMPLE I

Into a reaction flask was placed 51.6 g. of ethylene diamine followed by 18.4 g. of methyllaurate (10:1 molar ratio) and 30.0 g. of methanol (30%). The reaction mixture was heated to 75° C. for 26 hours at which time the methyllaurate was determined by gas chromatography methods to be exhausted. Into a second flask was placed the same reactants under the same reaction conditions except that no methanol was utilized. Analysis of the reaction mixtures was done to determine the amount of 2-aminoethyldodecanamide and the amount of diamide by-product. The results are shown in Table I below:

TABLE I

| Effect of Methanol on Diamide Concentration | | |
|---|---|---|
| % methanol | Mole Ratio Amine/Ester | % Diamide |
| 0 | 10:1 | 9.1 |
| 30 | 10:1 | 5.0 |

As can readily be seen from the results, there is significantly less diamide formed in the reaction flask containing the methanol solvent.

EXAMPLE II

Into a reaction flask was placed 300.5 g. of ethylene diamine followed by 107.2 g. of methyllaurate (10:1 molar ratio) and 278.4 g. of methanol (40%) and the reaction mixture was heated to 75° C. Into a second flask was placed the same reactants under the same reaction conditions except that no methanol was utilized. The methyllaurate concentration was determined by gas chromatography methods to show the rate of consumption of the methyllaurate with the results being shown below in table II.

TABLE II

| Methanol Conc. (%) | Effect of Methanol on Reaction Rate | | | | | | | | |
|---|---|---|---|---|---|---|---|---|---|
| | % Methyllaurate Remaining with Time (hours) | | | | | | | | |
| | 2 | 3 | 4 | 5 | 5 | 10 | 12 | 13 | 15 | 17 |
| 0 | 96 | 88 | 67 | 63 | 47 | 40 | 21 | 18 | 10 | 5 |
| 40 | 74 | 63 | 37 | 30 | 20 | 9 | 3 | — | — | — |

The results above clearly demonstrate that the rate of the reaction is significantly enhanced by the presence of the methanol solvent.

EXAMPLE III

Following the procedure of Example I, various reaction mixtures were prepared at a temperature of 45° C. utilizing varying amounts of methanol and various ratios of ethylenediamine to methyllaurate. The reactions were carried out until the methyllaurate was consumed and the amount of diamide was determined. The results are shown below in Table III.

TABLE III

| Effect of Methanol on Diamide Concentration | | | | | |
|---|---|---|---|---|---|
| Mole Ratio | % Methanol | | | | |
| Ethylenediamine/Methyllaurate | 0 | 10 | 20 | 30 | 40 |
| 25:1 | 2.9 | 2.1 | 2.1 | 1.9 | 1.9 |
| 20:1 | 3.7 | 2.6 | 2.8 | 2.8 | 2.3 |
| 15:1 | 4.9 | 3.8 | 3.8 | 3.2 | 3.1 |
| 10:1 | 6.1 | 5.5 | 4.8 | 4.4 | 4.1 |
| 5:1 | 11.5 | 9.6 | 10.1 | 10.4 | 8.5 |
| 2:1 | 27.4 | 27.0 | 25.1 | 25.4 | 23.0 |

EXAMPLE IV

Following the procedure of Example I, various reaction mixtures were prepared at a temperature of 25° C. utilizing varying amounts of methanol and various ratios of ethylenediamine to methyllaurate and the concentrations of methyllaurate and diamide were observed at various time intervals. The results are shown below in Table IV:

TABLE IV

| Effect of Methanol on Methyllaurate Consumption and Diamide Concentration | | | | | | | |
|---|---|---|---|---|---|---|---|
| MOLE RATIO AMINE/ESTER | | TIME (DAYS) | | | | | % METHANOL |
| | | 1 | 2 | 3 | 4 | 7 | |
| 25:1 | % Methyllaurate Remaining | 27.3 | 6.2 | 1.2 | 1.1 | — | 40 |
| | % Diamide Formed | 1.1 | 1.7 | 1.8 | 2.1 | 2.6 | 40 |
| 15:1 | % Methyllaurate Remaining | 30.0 | 10.2 | 2.6 | 1.3 | — | 40 |
| | % Diamide Formed | 1.6 | 2.4 | 3.1 | 3.4 | 4.1 | 40 |
| 5:1 | % Methyllaurate Remaining | 47.6 | 26.2 | 15.5 | 6.3 | 1.0 | 40 |
| | % Diamide Formed | 2.3 | 4.1 | 7.5 | 9.4 | 11.5 | 40 |
| 25:1 | % Methyllaurate Remaining | 27.4 | 6.4 | 2.3 | 0.3 | — | 30 |
| | % Diamide Formed | 1.2 | 1.8 | 2.1 | 2.3 | 2.3 | 30 |
| 15:1 | % Methyllaurate Remaining | 30.4 | 10.0 | 2.8 | 1.1 | — | 30 |
| | % Diamide Formed | 1.5 | 1.8 | 2.5 | 3.3 | 3.9 | 30 |
| 5:1 | % Methyllaurate | 48.7 | 26.4 | 13.8 | 4.0 | — | 30 |

TABLE IV-continued
Effect of Methanol on Methyllaurate Consumption and Diamide Concentration

| MOLE RATIO AMINE/ESTER | | TIME (DAYS) 1 | 2 | 3 | 4 | 7 | % METHANOL |
|---|---|---|---|---|---|---|---|
| 25:1 | % Diamide Formed | 2.1 | 5.8 | 6.6 | 9.0 | 10.5 | 30 |
| | % Methyllaurate Remaining | 35.6 | 11.0 | 3.2 | — | — | 20 |
| 15:1 | % Diamide Formed | 1.0 | 1.9 | 2.3 | 2.4 | 2.4 | 20 |
| | % Methyllaurate Remaining | 35.4 | 17.4 | 4.2 | 0.6 | — | 20 |
| 5:1 | % Diamide Formed | 1.3 | 2.2 | 3.5 | 3.4 | 3.7 | 20 |
| | % Methyllaurate Remaining | 55.9 | 29.6 | 16.5 | 1.8 | — | 20 |
| 25:1 | % Diamide Formed | 1.5 | 5.1 | 5.8 | 6.9 | 8.1 | 20 |
| | % Methyllaurate Remaining | | 26.0 | 9.3 | 4.4 | — | 10 |
| 15:1 | % Diamide Formed | | 1.0 | 2.8 | 2.8 | 3.0 | 10 |
| | % Methyllaurate Remaining | 51.7 | 35.3 | 16.0 | 6.4 | 0.7 | 10 |
| 5:1 | % Diamide Formed | 1.2 | 1.8 | 2.6 | 3.0 | 4.8 | 10 |
| | % Methyllaurate Remaining | 70.4 | 48.0 | 25.8 | 17.3 | 1.0 | 10 |
| 25:1 | % Diamide Formed | 1.0 | 3.2 | 4.3 | 4.7 | 7.8 | 10 |
| | % Methyllaurate Remaining | 81.0 | 66.5 | 44.9 | 36.7 | 19.1 | 0 |
| 15:1 | % Diamide Formed | — | 0.4 | 0.9 | 1.3 | 2.4 | 0 |
| | % Methyllaurate Remaining | 87.5 | 84.5 | | 48.9 | 25.9 | 0 |
| 5:1 | % Diamide Formed | — | — | | 1.2 | 3.3 | 0 |
| | % Methyllaurate Remaining | 88.3 | 84.0 | | 61.2 | 34.4 | 0 |
| | % Diamide Formed | 0.1 | 0.3 | | 1.9 | 5.3 | 0 |

EXAMPLE V

Into a reaction flask was placed 67.9 g. ethylene diamine, 12.1 g. methyllaurate (20:1 molar ratio) and 20.0 g. ethanol (20%) and heated to 45° C. The reaction was determined to be complete on the fourth day and 2.7% diamide was found to be present utilizing gas chromatographic methods. When the same reaction was carried out in the absence of a solvent, the diamide level was found to be 4.6%.

EXAMPLE VI

The reaction of Example V was carried out utilizing isopropanol instead of ethanol. The reaction was determined to be complete on the fifth day and 3.3% diamide was found to be present utilizing gas chromatographic methods. When the same reaction was carried out in the absence of a solvent, the diamide level was found to be 4.6%.

EXAMPLE VII

Into a reaction flask was placed 54.2 g. ethylenediamine, 25.8 g. methyltallowate (10:1 molar ratio) and 20.0 g. methanol and heated to 45° C. In a second flask was placed 40.7 g. ethylene diamine, 19.3 g. of methyltallowate and 40.0 g. of methanol and heated to 45° C. Into a third flask was placed 67.7 g. of methanol and 37.3 g. of methyltallowate (10:1 molar ratio) and no solvent. The reactions were determined to be completed on the fourth day, third day and seventh day respectively and 2.2%, 1.3% and 2.6% diamide were found to be present, respectively.

What is claimed is:

1. A process for the preparation of monoacyl polyalkylene polyamines of the formula

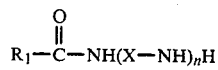

wherein $R_1$ is straight or branched chain alkyl of from 7 to 21 carbon atoms or mixtures thereof, n is an integer of from 1 to 3 and X is straight or branched chain alkylene or hydroxyalkylene of from 2 to 6 carbon atoms, comprising reacting a fatty acid ester of the formula

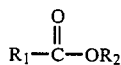

wherein $R_1$ is as above and $R_2$ is lower alkyl of from 1 to 3 carbon atoms, with a polyalkylene polyamine of the formula

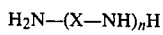

wherein X and n are as above, in the presence of from about 5 to 40% by weight of the total weight of the reaction mixture of a hydroxylic solvent and at a temperature of from about 20° C. to 80° C. or under pressure.

2. The process of claim 1 wherein the hydroxylic solvent is selected from the group consisting of methanol, ethanol and isopropanol.

3. The process of claim 2 wherein the hydroxylic solvent is methanol.

4. The process of claim 1 wherein the polyalkylene polyamine and fatty acid ester are present in a mole ratio of from about 25:1 to 5:1.

5. The process of claim 4 wherein the polyalkylene polyamine and fatty acid ester are present in a mole ratio of from about 20:1 to 10:1.

* * * * *